United States Patent
Inui et al.

(10) Patent No.: US 6,632,959 B2
(45) Date of Patent: Oct. 14, 2003

(54) BASIC CATALYSTS AND PROCESS FOR PRODUCING CARBONYL COMPOUND DERIVATIVES

(75) Inventors: Kan-ichiro Inui, Kimitsu (JP); Shunji Oshima, Ichihara (JP); Toru Kurabayashi, Ichihara (JP); Sakae Kawamura, Ichihara (JP); Masahiro Yokota, Ichihara (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/485,238

(22) PCT Filed: Aug. 5, 1998

(86) PCT No.: PCT/JP98/03488

§ 371 (c)(1), (2), (4) Date: Feb. 7, 2000

(87) PCT Pub. No.: WO99/07468

PCT Pub. Date: Feb. 8, 1999

(65) Prior Publication Data

US 2002/0169069 A1 Nov. 14, 2002

(30) Foreign Application Priority Data

Aug. 7, 1997 (JP) .............................................. 9-213666

(51) Int. Cl.[7] .......................... C07C 67/00; C07C 67/48; C07C 67/02
(52) U.S. Cl. ....................... 560/238; 502/103; 560/248; 560/252
(58) Field of Search ......................... 502/103; 562/174; 560/238, 248, 252

(56) References Cited

U.S. PATENT DOCUMENTS

| | | | |
|---|---|---|---|
| 3,091,632 A | 5/1963 | Hagemeyer et al. | 560/105 |
| 4,127,470 A | * 11/1978 | Baird, Jr. et al. | 208/58 |
| 4,657,890 A | 4/1987 | Garces et al. | 502/340 |
| 4,883,906 A | * 11/1989 | Argyropoulos et al. | 560/238 |
| 4,939,312 A | 7/1990 | Baerns et al. | 585/500 |
| 5,206,414 A | 4/1993 | Evans et al. | 560/75 |
| 5,567,826 A | 10/1996 | Knebel et al. | 548/324.1 |

FOREIGN PATENT DOCUMENTS

| | | |
|---|---|---|
| EP | 0 186 076 | 7/1986 |
| EP | 0 707 887 | 4/1996 |
| GB | 1 259 766 | 1/1972 |
| JP | 55-153743 | 11/1980 |
| JP | 58-65245 | 4/1983 |
| JP | 6-343862 | 12/1994 |
| JP | 9-169687 | 6/1997 |

OTHER PUBLICATIONS

Catalysis Science and Technology, Edited by John R. Anderson and Michel Boudart, vol. 2, Springer–Verlag, Berlin Heidelberg New York 1981, page with Table 1 (Solid acids) and Table 2 (Solid bases) thereon.

* cited by examiner

Primary Examiner—Alan L. Rotman
Assistant Examiner—Taylor V. Oh
(74) Attorney, Agent, or Firm—Wenderoth, Lind & Ponack, L.L.P.

(57) ABSTRACT

A base catalyst, obtained by formulating at least one alkali metal compound selected from the group consisting of alkoxides, hydroxides and oxides of alkali metals and an alkaline-earth metal oxide in a ratio of "the weight of alkaline metal compound/the weight of alkaline-earth metal oxide"=0.005 to 1, is used in a reaction of an aldehyde to produce a glycol monoester, thereby providing a base catalyst with an improved efficiency which can be applied to aldol reaction or the like and which has high activity to give target product in a high selectivity.

13 Claims, No Drawings

BASIC CATALYSTS AND PROCESS FOR PRODUCING CARBONYL COMPOUND DERIVATIVES

This application is a 371 application of PCT/JP98/03488 filed Aug. 5, 1998.

TECHNICAL FIELD

The present invention relates to a base catalyst and to a method for producing a derivative of carbonyl compound using the same. More particularly, the present invention relates to a base catalyst comprising an alkali metal compound selected from the group consisting of alkoxides, hydroxides and oxides of alkali metals and an alkaline-earth metal oxide, and to a method for producing a derivative of carbonyl compound, such as glycol monoesters or the like, from aldehydes using the catalyst.

BACKGROUND ART

Base catalysts are used in synthetic reactions, such as aldol condensation reaction, for producing many kinds of compounds. When reactions are conducted on an industrial scale using base catalysts, there have been widely used alkali metal hydroxides, typically sodium hydroxide, and alkali metal alkoxides, typically sodium methoxide.

However, most of the alkali metal hydroxides and alkoxides act as a homogeneous catalyst in the reaction system and, hence, they require neutralization and washing with water as operations for removing the catalyst after completion of the reaction. This naturally results in the production of a large amount of waste water. In general, homogeneous catalysts produce larger amounts of by-products, so that it is often the case that a selectivity of the product (selectivity of the target product) is lowered.

On the other hand, in Japanese Patent Application Laid-open No 58-65245, a method in which an alkaline-earth metal oxide is used as a solid base catalyst in a method for producing a glycol monoester from an aldehyde with a solid base catalyst is described. However, reactions with barium oxide or magnesium oxide alone, for example, could afford low levels of catalytic activity so that it has been difficult to provide sufficient catalytic activity by using alkaline-earth metal oxides alone.

As described above, with conventional catalyst systems, use of homogeneous catalysts having higher activity has caused a larger amount of waste water whereas use of heterogeneous catalysts has caused only a small amount of waste water, but it has made it difficult to obtain sufficient catalyst activity or product selectivity.

Generally, use of heterogeneous solid catalysts, as compared to homogeneous catalyst reactions, provides the following advantages.
(1) There is no need for such operations as neutralization, washing with water, or the like of the catalyst, resulting in the production of no or much less waste water.
(2) The catalyst can be reused.
(3) Product selectivity is high in most cases.

Therefore, it can be expected that methods which involve use of heterogeneous solid catalysts are simpler in process, less inexpensive in cost for a plant, and higher in yield of the target product as compared with those methods using homogeneous catalysts to obtain the target products. Further, because of generating no or much less waste water as compared with the latter methods using homogeneous catalysts, the former methods not only yield less cost for disposal of waste water but also enable suppression of adverse effects on environment, of which a problem has been arisen recently.

However, as stated above, none of the conventional heterogeneous solid catalysts could present sufficient catalytic activity nor sufficient product selectivity and, hence, a further technical innovation has been needed.

DISCLOSURE OF THE INVENTION

It is an object of the present invention to solve the above-described problems and provide an efficient base catalyst which can be applied to base catalyst reactions generally employed, for example, aldol reaction, Michael addition reaction, Tishchenko reaction and the like and which can produce a target product at high activity and high selectivity.

Previously, the present inventors completed an invention on a method for producing carbonyl compound derivatives using a solid base catalyst comprising barium and calcium (Japanese Patent Application Laid-open No 8-29979) and their further study revealed that use of an alkaline-earth metal oxide which is a conventional solid base catalyst, in combination with a minute amount of an alkali metal compound as catalysts and of a two-step reaction with employing the alkali metal compound as a catalyst in the earlier reaction step and the alkaline-earth metal oxide in the later reaction step increases the catalytic activity, which allows a remarkable decrease in the amount of the catalyst to be used, and an increase in product selectivity, and suppresses generation of waste water to a minimum level, thus completing the present invention.

That is, the base catalyst of the present invention comprises at least one alkali metal compound selected from the group consisting of alkoxides, hydroxides and oxides of alkali metals and an alkaline-earth metal oxide with a weight ratio of the alkali metal compound to the alkaline-earth metal oxide, which is calculated by a formula, "the weight of alkaline metal compound/the weight of alkaline-earth metal oxide", being from 0.005 to 1.

The method for producing a derivative of carbonyl compound according to the present invention is a method for producing a derivative of carbonyl compound from a carbonyl compound in the presence of a catalyst wherein the catalyst is a catalyst comprising at least one alkali metal compound selected from the group consisting of alkoxides, hydroxides and oxides of alkali metals and an alkaline-earth metal oxide.

Another method for producing a derivative of carbonyl compound according to the present invention comprises an earlier reaction step in which at least one alkali metal compound selected from the group consisting of alkoxides, hydroxides and oxides of alkali metals is used as the catalyst, and a later reaction step in which an alkaline-earth metal oxide is used as the catalyst.

When the reaction is carried out with an alkali metal compound alone as a catalyst, high catalytic activity is obtained while product selectivity is insufficient. In contrast, use of an alkaline-earth metal oxide alone results in a decreased reactivity. The base catalyst of the present invention is a base catalyst which comprises an alkali metal compound and an alkaline-earth metal oxide in combination in a specified weight ratio, can provide high catalytic activity and excellent product selectivity simultaneously and generates less waste water.

Hereafter, embodiments of the present invention will be described.

(1) Base Catalyst

The base catalyst of the present invention comprises an alkali metal compound and an alkaline-earth metal oxide.

The alkali metal compound of the present invention is selected from the group consisting of alkali metal alkoxides, alkali metal hydroxides and alkali metal oxides. The alkali metals include preferably sodium, potassium and lithium but are not limited thereto.

As the alkali metal alkoxides, there can be used those whose alkyl group contains 1 to 12 carbon atoms. Specific examples thereof include sodium methoxide, sodium ethoxide, sodium t-butoxide, potassium methoxide, potassium ethoxide, potassium t-butoxide, lithium methoxide, lithium ethoxide, lithium t-butoxide, etc.

As the alkali metal hydroxides, there can be used, preferably sodium hydroxide, potassium hydroxide, lithium hydroxide, etc. And as the alkali metal oxides, there can be used preferably sodium oxide, potassium oxide, lithium oxide, etc.

The alkaline-earth metals in the alkaline-earth metal oxides of the present invention include magnesium, calcium, barium and strontium, preferably calcium, barium and strontium, particularly preferably barium and strontium, but are not limited thereto. Specific examples of the alkaline-earth metal oxides include calcium oxide, barium oxide and strontium oxide.

The weight ratio of the alkali metal compound to the alkaline-earth metal oxide in the base catalyst of the present invention is such that alkali metal compound/alkaline-earth metal oxide=0.005 to 1, preferably, 0.01 to 0.5 (weight ratio). When this ratio is too small, the catalytic activity of the base catalyst as a whole tends to become low, whereas when it is too large, the product selectivity tends to decrease.

The alkali metal compounds used in the present invention may be in any form, such as powder, particle, mass, liquid, and the like. And the alkaline-earth metal oxide used in the present invention may be in any form, such as powder, particle, mass, and the like. Among the forms, preferred one is a combination of a liquid alkali metal compound and a solid alkaline-earth metal oxide.

The base catalyst of the present invention, containing a combination of a solid alkaline-earth metal oxide and an alkali metal compound which acts in the form of a liquid in the reaction system in appropriate amounts, can overcome high cost and low catalytic activity which are disadvantages of the alkaline-earth metal oxides, and also can suppress to a minimum level the generation of a large amount of waste water accompanying neutralization and washing with water and overcome the low selectivity of target compound which are disadvantages of the alkali metal compounds.

As the alkali metal compounds and alkaline-earth metal oxides, i.e., the components of the base catalyst of the present invention, there can be used commercially available ones as they are. Further, as for the method for preparing the base catalyst, there can be used known methods, for example, a method in which an alkali metal compound and an alkaline-earth metal oxide are mixed by a known means.

Since it comprises the alkali metal compound and alkaline-earth metal oxide, the base catalyst of the present invention may be used in any form of use as far as the both are employed in combination. For example, the alkali metal compound and alkaline-earth metal oxide may be simultaneously or previously mixed and formulated so that they can be added in the lump to the reaction system. Alternatively, the components of the catalyst may be used in two steps separately, in such a manner that the reaction is carried out using the alkali metal compound at the first step and using the alkaline-earth metal oxide at the second step.

While the base catalyst of the present invention can be used in general base catalyst reactions, it can be used advantageously in producing preferably derivatives of carbonyl compound from carbonyl compounds. In particular, it exhibits considerable effects when used in producing 2,2,4-trimethyl-1,3-pentanediol monoisobutyrate from isobutyraldehyde but the present invention is not limited thereto.

(2) Production Method of Carbonyl Compound Derivatives

The production method of the present invention is to produce a derivative of carbonyl compound from a carbonyl compound in the presence of a catalyst which comprises an alkali metal compound and an alkaline-earth metal oxide. The alkali metal compound and the alkaline-earth metal oxide which are used may be those employed in the base catalyst described above. The weight ratio of the alkali metal compound and the alkaline-earth metal oxide in the above-described catalyst is not limited particularly but the above-described base catalyst wherein the weight ratio of them is such that alkali metal compound/alkaline-earth metal oxide= 0.005 to 1, more preferably 0.01 to 0.5 (weight ratio) is used preferably.

The carbonyl compounds used as starting materials in the production method of the present invention are not limited particularly as far as they are organic compounds having a carbonyl group and include, for example, aldehydes and ketones, preferably aldehydes, more preferably aldehydes having 2 to 12 carbon atoms, particularly preferably aliphatic aldehydes having 4 to 8 carbon atoms. More specifically, the aliphatic aldehydes include isobutyraldehyde, n-butyraldehyde, 2-ethylbutyraldehyde, 2-ethylhexylaldehyde, and the like. As the ketone, there can be cited acetone. However, the present invention is not limited to these compounds.

As the method for producing the carbonyl compound derivatives from carbonyl compounds according to the present invention, there can be cited those that involve reactions which can proceed on the carbonyl compounds as starting compounds, in the presence of base catalysts, such as aldol condensation reaction, Tishchenko reaction, Michael addition reaction, and the like.

For example, there can be cited a method for producing glycol monoesters from aldehydes, a method for producing β-hydroxy aldehydes or α,β-unsaturated aldehydes from aldehydes, or the like. Therefore, the carbonyl compound derivatives produced by the method of the present invention can include glycol monoesters, β-hydroxy aldehydes, α,β-unsaturated aldehydes, and the like, which are produced from carbonyl compounds by the above-described reactions.

More preferred one is a method for producing glycol monoesters represented by general formula (II) from aldehydes represented by general formula (I):

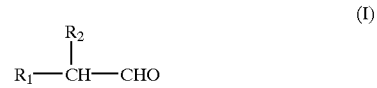

(I)

wherein, $R_1$ and $R_2$ in formula (I), which may be same or different, independently represent an alkyl group having 1 to 5 carbon atoms, preferably 1 to 3 carbon atoms;

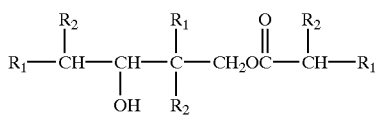

wherein, $R_1$, and $R_2$ in formula (II) have the same meanings as defined in formula (I).

The method of the present invention is highly effective particularly in the method of producing 2,2,4-trimethyl-1,3-pentanediol monoisobutyrate as a carbonyl compound derivative from isobutyraldehyde as a carbonyl compound (in formulae (I) and (II) above, $R_1$, and $R_2$ are each a methyl group) but the present invention is not limited thereto.

The carbonyl compound as a starting material is preferably those which contain less acid and water which are contained as impurities. However, the carbonyl compound with an acid content of 0.1% by weight or less and a water content of 0.1% by weight or less may be well used in the present invention.

The production method of the present invention may be carried out either as a continuous process or as a batch process. Usually, the reaction is carried out preferably under inert atmosphere such as nitrogen and the like in a reaction vessel equipped with a stirrer.

As the method of addition of the base catalyst to the reaction system, there can be cited a method in which the alkali metal compound and alkaline-earth metal oxide are added in the lump and stirred together with the carbonyl compound as a starting material to proceed the reaction in one step, for example, simultaneous incorporation of the alkali metal compound and the alkaline-earth metal oxide in the reaction vessel or mixing and preparing them in advance before they can be incorporated into the reaction vessel.

It is also possible to adopt a 2-step addition method in which the alkali metal compound is added first followed by addition of the alkaline-earth metal oxide. That is, the reaction may be divided into two steps, i.e., earlier reaction step and later reaction step, with using as a catalyst the alkali metal compound in the earlier reaction step and the alkaline-earth metal oxide in the later reaction step to complete the reaction.

Accordingly, a preferred production method according to the present invention comprises an earlier reaction step using at least one alkali metal compound selected from the group consisting of alkoxides, hydroxides and oxides of alkali metals as a catalyst and a later reaction step using an alkaline-earth metal oxide as a catalyst. Here, use of the alkaline-earth metal oxide in the earlier reaction step and the alkali metal compound in the later reaction step is not preferable since the reactivity tends to decrease.

The method of diving the reaction in two steps and adding different catalysts in different steps separately (hereafter, sometimes referred to as "two-step reaction method") has the following advantages. That is, it is otherwise necessary to add an excess amount of catalyst taking into consideration of deactivation of the catalyst added due to the moisture which the carbonyl compound used as a starting material contains not a little. On the other hand, alkaline-earth metal oxides such as barium oxide and the like are more expensive than alkali metal compounds and therefore there has been a problem that adding the alkaline-earth metal oxides in the reaction system from the beginning results in using them in excess amounts, which is costly. According to the two-step reaction method of the present invention, first an alkali metal compound, which is inexpensive, is added to the reaction system to kill the moisture therewith, and subsequently the alkaline-earth metal oxide is added to run the reaction, so that the amount of using of the expensive alkaline-earth metal oxide can be minimized, which makes the system economically competitive. Since the effects of moisture can be removed reliably and for some reasons, the method of the present invention can provide, with good reproducibility and stably, conversion ratio into the target product and, selectivity and yield for the target product superior to those of the conventional methods.

In the two-step reaction method, the timing at which the alkali metal compound and the alkaline-earth metal oxide are added may be decided appropriately and empirically depending on the kind and water content of carbonyl compound to be used, and so on, but preferably the reaction time for the earlier reaction step using the alkali metal compound lasts 0.1 to 2 hours and that for the later reaction step using the alkaline-earth metal oxide lasts for 0.2 to 3 hours. Therefore, it is preferred to decide the timing of addition of the respective catalyst components such that the respective steps can be run in the above-mentioned reaction times.

The weight ratio of the alkali metal compound and alkaline-earth metal oxide in the two-step reaction method is not limited particularly but is preferably such that alkali metal compound/alkaline-earth metal oxide=0.005 to 1, more preferably 0.01 to 0.5 (weight ratio), as in the above-described one-step reaction.

In the production method of the present invention, for the one-step reaction, it is possible to use a catalyst comprising a combination of an alkali metal compound and an alkaline earth metal oxide in an amount of 0.01 to 20% by weight, preferably 0.05 to 5% by weight, based on the weight of the reaction liquid i.e. the carbonyl compound used as the starting material, but the present invention is not limited thereto.

Further, in the above-described two-step reaction method, it is preferred to use the alkali metal compound within the ranges of 0.001 to 0.1% by weight and the alkaline-earth metal oxide within the ranges of 0.01 to 10% by weight based on the weight of the reaction liquid but the present invention is not limited thereto.

In the production method of the present invention, the reaction temperature at which the above-described catalyst is used is selected from the ranges of preferably 10 to 130° C. For example, when the reaction is run in a batch process, a mixture of the catalyst and the reaction liquid is kept at 10 to 130° C. for 0.3 to 5 hours. At temperatures below 10° C., the reaction rate is insufficient whereas the product selectivity is aggravated at temperatures above 130° C.

For the one-step reaction, it is more preferable to select the reaction temperature from the ranges of 40 to 100. For example, when the reaction is carried out in a batch process, a mixture of the catalyst and reaction liquid is kept at 40 to 100° C. for 0.3 to 5 hours.

Further, for the two-step reaction method, it is preferred that the earlier reaction step be run at a reaction temperature of 10 to 70° C. for 0.1 to 2 hours and the later reaction step be carried out at a reaction temperature of 50 to 100° C. for 0.2 to 3 hours.

After the reaction is completed, the target product can be obtained from the reaction mixture, for example, by washing the reaction mixture with a minute amount of water and distilling it by a known method.

BEST MODE FOR CARRYING OUT THE INVENTION

Hereafter, examples of the present invention will be described.

EXAMPLE 1

0.08 g of sodium methoxide (MeONa, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 2 hours. After completion of the reaction, the reaction mixture was analyzed by gas chromatography. The results obtained are shown below. Note that 2,2,4-trimethyl-1,3-pentanediol monoisobutyrate will hereafter be referred to as "CS-12".

| | |
|---|---|
| Conversion ratio of isobutyraldehyde: | 96.8% |
| Selectivity of CS-12: | 94.3% |
| Yield of CS-12: | 91.3% |

EXAMPLE 2

0.06 g of sodium methoxide (MeONa, manufactured by Wako Pure Chemical Industries, Ltd.) was added to 0.6 g of strontium oxide (SrO, manufactured by Merck) and the total amount thereof was transferred to a reaction vessel. 600 g of isobutyraldehyde was added thereto and reacted at 70° C. for 2.5 hours. After completion of the reaction, the reaction mixture was analyzed by gas chromatography. The results obtained are shown below.

| | |
|---|---|
| Conversion ratio of isobutyraldehyde: | 93.2% |
| Selectivity of CS-12: | 95.3% |
| Yield of CS-12: | 88.8% |

EXAMPLE 3

0.07 g of sodium ethoxide (EtONa, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 1 hour. After completion of the reaction, the reaction mixture was analyzed by gas chromatography. The results obtained are shown below.

| | |
|---|---|
| Conversion ratio of isobutyraldehyde: | 93.8% |
| Selectivity of CS-12: | 94.0% |
| Yield of CS-12: | 88.2% |

EXAMPLE 4

0.09 g of potassium ethoxide (EtOK, manufactured by Aldrich) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 2 hours. After completion of the reaction, the reaction mixture was analyzed by gas chromatography. The results obtained are shown below.

| | |
|---|---|
| Conversion ratio of isobutyraldehyde: | 95.7% |
| Selectivity of CS-12: | 92.2% |
| Yield of CS-12: | 88.2% |

EXAMPLE 5

0.08 g of lithium methoxide (MeOLi, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 2 hours. After completion of the reaction, the reaction mixture was analyzed by gas chromatography. The results obtained are shown below.

| | |
|---|---|
| Conversion ratio of isobutyraldehyde: | 93.6% |
| Selectivity of CS-12: | 94.3% |
| Yield of CS-12: | 88.3% |

EXAMPLE 6

0.11 g of sodium t-butoxide (t-BuONa, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 1.5 hours. After completion of the reaction, the reaction mixture was analyzed by gas chromatography. The results obtained are shown below.

| | |
|---|---|
| Conversion ratio of isobutyraldehyde: | 95.3% |
| Selectivity of CS-12: | 93.9% |
| Yield of CS-12: | 89.5% |

EXAMPLE 7

0.11 g of potassium t-butoxide (t-BuOK, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 2 hours. After completion of the reaction, the reaction mixture was analyzed by gas chromatography. The results obtained are shown below.

| | |
|---|---|
| Conversion ratio of isobutyraldehyde: | 96.4% |
| Selectivity of CS-12: | 93.0% |
| Yield of CS-12: | 89.7% |

EXAMPLE 8

0.06 g of sodium hydroxide (NaOH, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 5 hours. After completion of the reaction, the reaction mixture was analyzed by gas chromatography. The results obtained are shown below.

| | |
|---|---|
| Conversion ratio of isobutyraldehyde: | 91.5% |
| Selectivity of CS-12: | 94.8% |
| Yield of CS-12: | 86.7% |

EXAMPLE 9

0.06 g of potassium hydroxide (KOH, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 3 hours. After completion of the reaction, the reaction mixture was analyzed by gas chromatography. The results obtained are shown below.

| | |
|---|---|
| Conversion ratio of isobutyraldehyde: | 88.7% |
| Selectivity of CS-12: | 95.2% |
| Yield of CS-12: | 84.4% |

EXAMPLE 10

0.12 g of sodium hydroxide (NaOH, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 3 hours. After completion of the reaction, the reaction mixture was analyzed by gas chromatography. The results obtained are shown below.

| | |
|---|---|
| Conversion ratio of isobutyraldehyde: | 78.6% |
| Selectivity of CS-12: | 95.1% |
| Yield of CS-12: | 74.7% |

EXAMPLE 11

0.15 g of sodium oxide ($Na_2O$, manufactured by Aldrich) was added to 1.5 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 3.5 hours. After completion of the reaction, the reaction mixture was analyzed by gas chromatography. The results obtained are shown below.

| | |
|---|---|
| Conversion ratio of isobutyraldehyde: | 90.3% |
| Selectivity of CS-12: | 92.5% |
| Yield of CS-12: | 83.5% |

EXAMPLE 12

0.005 g of sodium methoxide (MeONa, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 5 hours. After completion of the reaction, the reaction mixture was analyzed by gas chromatography. The results obtained are shown below.

| | |
|---|---|
| Conversion ratio of isobutyraldehyde: | 89.3% |
| Selectivity of CS-12: | 92.2% |
| Yield of CS-12: | 82.3% |

EXAMPLE 13

0.6 g of sodium methoxide (MeONa, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 50° C. for 1 hour. After completion of the reaction, the reaction mixture was analyzed by gas chromatography. The results obtained are shown below.

| | |
|---|---|
| Conversion ratio of isobutyraldehyde: | 97.5% |
| Selectivity of CS-12: | 90.1% |
| Yield of CS-12: | 87.8% |

EXAMPLE 14

0.015 g of sodium oxide ($Na_2O$, manufactured by Aldrich) was added to 1.5 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 3.5 hours. After completion of the reaction, the reaction mixture was analyzed by gas chromatography. The results obtained are shown below.

| | |
|---|---|
| Conversion ratio of isobutyraldehyde: | 96.4% |
| Selectivity of CS-12: | 93.5% |
| Yield of CS-12: | 90.1% |

EXAMPLE 15

500 g of the reaction mixture obtained in Example 1 was taken, 10 g of water was added thereto, and it was rectified by a known method after oil-water separation. The results obtained are shown below.

| | |
|---|---|
| Yield of CS-12: | 443.5 g |
| Rectification efficiency: | 88.7% |

Comparative Example 1

After 4.0 g of magnesium oxide (MgO, manufactured by Wako Pure Chemical Industries, Ltd.) was burned at 700° C. for 1 hour in vacuum, it was cooled down to room temperature. The total amount thereof was transferred to a reaction vessel and 200.0 g of isobutyraldehyde was added thereto and reacted at 110° C. for 15 hours. After completion of the reaction, the reaction mixture was analyzed by gas chromatography. The results obtained are shown below.

| | |
|---|---|
| Conversion ratio of isobutyraldehyde: | 0.1% |
| Selectivity of CS-12: | 90.5% |
| Yield of CS-12: | 0.1% |

Comparative Example 2

3.0 g of barium oxide (BaO, manufactured by Wako Pure Chemical Industries, Ltd.) and 600 g of isobutyraldehyde were charged in a reaction vessel and the mixture was stirred and reacted at 70° C. for 5 hours. After completion of the reaction, the reaction mixture was analyzed by gas chromatography. The results obtained are shown below.

| | |
|---|---|
| Conversion ratio of isobutyraldehyde: | 34.1% |
| Selectivity of CS-12: | 84.7% |
| Yield of CS-12: | 28.9% |

Comparative Example 3

After 3.7 g of calcium oxide ($CaCO_3$, manufactured by Wako Pure Chemical Industries, Ltd.) was burned at 900° C. for 1 hour in vacuum, it was transferred to a reaction vessel and 200 g of isobutyraldehyde was added thereto and reacted at 60° C. for 2.6 hours. After completion of the reaction, the reaction mixture was analyzed by gas chromatography. The results obtained are shown below.

| | |
|---|---|
| Conversion ratio of isobutyraldehyde: | 94.5% |
| Selectivity of CS-12: | 56.2% |
| Yield of CS-12: | 53.1% |

Comparative Example 4

0.5 g of sodium hydroxide (NaOH, manufactured by Wako Pure Chemical Industries, Ltd.) was added to 0.3 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 3 hours. After completion of the reaction, the reaction mixture was analyzed by gas chromatography. The results obtained are shown below.

| | |
|---|---|
| Conversion ratio of isobutyraldehyde: | 98.5% |
| Selectivity of CS-12: | 23.6% |
| Yield of CS-12: | 23.2% |

Comparative Example 5

0.002 g of sodium hydroxide (NaOH, manufactured by Wako Pure Chemical Industries, Ltd.) was added to 0.6 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 5 hours. After completion of the reaction, the reaction mixture was analyzed by gas chromatography. The results obtained are shown below.

| | |
|---|---|
| Conversion ratio of isobutyraldehyde: | 17.3% |
| Selectivity of CS-12: | 73.5% |
| Yield of CS-12: | 12.7% |

Comparative Example 6

0.5 g of sodium methoxide (MeONa, manufactured by Wako Pure Chemical Industries, Ltd.) was added to 0.3 g of barium oxide (BaO, manufactured by Wako Pure Chemical Industries, Ltd.) and the total amount thereof was transferred to a reaction vessel. 600 g of isobutyraldehyde was added thereto and reacted at 70° C. for 2 hours. After completion of the reaction, the reaction mixture was analyzed by gas chromatography. The results obtained are shown below.

| | |
|---|---|
| Conversion ratio of isobutyraldehyde: | 98.1% |
| Selectivity of CS-12: | 25.1% |
| Yield of CS-12: | 24.6% |

Comparative Example 7

0.002 g of sodium methoxide (MeONa, manufactured by Wako Pure Chemical Industries, Ltd.) was added to 0.6 g of barium oxide (BaO, manufactured by Wako Pure Chemical Industries Ltd.) and the total amount thereof was transferred to a reaction vessel. 600 g of isobutyraldehyde was added thereto and reacted at 70° C. for 4 hours. After completion of the reaction, the reaction mixture was analyzed by gas chromatography. The results obtained are shown below.

| | |
|---|---|
| Conversion ratio of isobutyraldehyde: | 20.1% |
| Selectivity of CS-12: | 79.2% |
| Yield of CS-12: | 15.9% |

Comparative Example 8

0.3 g of sodium methoxide (MeONa, manufactured by Wako Pure Chemical Industries, Ltd.) was added to 600 g of isobutyraldehyde and reacted at 70° C. for 1.5 hours. After completion of the reaction, the reaction mixture was analyzed by gas chromatography. The results obtained are shown below.

| | |
|---|---|
| Conversion ratio of isobutyraldehyde: | 95.1% |
| Selectivity of CS-12: | 80.7% |
| Yield of CS-12: | 76.7% |

Comparative Example 9

39.2 g of calcium hydroxide ($Ca(OH)_2$, manufactured by Kanto Kagaku) was suspended in 100 ml of pure water. 0.5 g of barium nitrate ($Ba(NO_3)_2$, manufactured by Wako Pure Chemical Industries, Ltd.) was dissolved in 200 ml of pure water. The solution was added to the suspension of calcium hydroxide and mixed followed by drying to form 4.0 g of white solid, which then was burned at 700° C. for 1 hour in vacuum and cooled to room temperature. As a result, 3.9 g of a catalyst containing 2% by weight of barium was obtained. The total amount of the resulting catalyst was transferred to a reaction vessel. 200.0 g of isobutyraldehyde was added thereto and the mixture was reacted at 110° C. for 1 hour. After completion of the reaction, the reaction mixture was filtered and the filtrate was analyzed by gas chromatography. The results obtained are shown below.

| | |
|---|---|
| Conversion ratio of isobutyraldehyde: | 90.9% |
| Selectivity of CS-12: | 83.8% |
| Yield of CS-12: | 76.2% |

Comparative Example 10

122.6 g of calcium nitrate tetrahydrate ($Ca(NO_3)_2 \cdot 4H_2O$, manufactured by Wako Pure Chemical Industries, Ltd.) and 1.7 g of barium nitrate ($Ba(NO_3)_2$, manufactured by Wako Pure Chemical Industries, Ltd.) were dissolved in 500 ml of pure water. A solution of 60.6 g of ammonium carbonate (($NH_4)_2CO_3$, manufactured by Wako Pure Chemical Industries, Ltd.) in 300 ml of pure water was added to the resulting solution. The precipitates formed were filtered, washed with water, and dried to obtain a precursor of catalyst. 7.3 g of white solid thus obtained was burned at 900° C. for 1 hour in vacuum, the total amount thereof was transferred to a reaction vessel, and 200.0 g of isobutyraldehyde was added thereto. Then, the mixture was stirred and reacted at 60° C. for 0.5 hour. After completion of the reaction, the reaction mixture was filtered and the filtrate was analyzed by gas chromatography. The results obtained are shown below.

| | |
|---|---|
| Conversion ratio of isobutyraldehyde: | 98.8% |
| Selectivity of CS-12: | 93.8% |
| Yield of CS-12: | 92.7% |

Comparative Example 11

10 g of sodium hydroxide (NaOH, manufactured by Wako Pure Chemical Industries, Ltd.) was added to 600 g of isobutyraldehyde and the mixture was stirred and reacted at 70° C. for 2 hours. 500 g of this solution was taken out and 100 g of water was added thereto. The mixture was rectified by a known method after oil-water separation. The results obtained are shown below.

| | |
|---|---|
| (After reaction) | |
| Conversion ratio of isobutyraldehyde: | 75.0% |
| Selectivity of CS-12: | 90.2% |
| Yield of CS-12: | 67.7% |
| (After rectification) | |
| Yield of CS-12: | 248.6 g |
| Rectification efficiency: | 49.7% |

EXAMPLE 16

0.08 g of sodium methoxide (MeONa, manufactured by Wako Pure Chemical Industries, Ltd.) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 2.5 hours. The reaction mixture after completion of the reaction was analyzed by gas chromatography. The results obtained are shown below.

| | |
|---|---|
| Conversion ratio of isobutyraldehyde: | 95.3% |
| Selectivity of CS-12: | 92.6% |
| Yield of CS-12: | 88.2% |

EXAMPLE 17

0.08 g of sodium methoxide (MeONa, manufactured by Wako Pure Chemical Industries, Ltd.) was added to 600 g of isobutyraldehyde and reacted at 40° C. for 1 hour. Subsequently, 0.3 g of strontium oxide (SrO, manufactured by Merck) was added thereto and reacted at 70° C. for 3.5 hours. The reaction mixture after completion of the reaction was analyzed by gas chromatography. The results obtained are shown below.

| | |
|---|---|
| Conversion ratio of isobutyraldehyde: | 95.7% |
| Selectivity of CS-12: | 90.7% |
| Yield of CS-12: | 86.8% |

EXAMPLE 18

0.07 g of sodium ethoxide (EtONa, manufactured by Wako Pure Chemical Industries, Ltd.) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 2 hours. The reaction mixture after completion of the reaction was analyzed by gas chromatography. The results obtained are shown below.

| | |
|---|---|
| Conversion ratio of isobutyraldehyde: | 96.8% |
| Selectivity of CS-12: | 92.9% |
| Yield of CS-12: | 89.9% |

EXAMPLE 19

0.09 g of potassium ethoxide (EtOK, manufactured by Aldrich) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 2.5 hours. The reaction mixture after completion of the reaction was analyzed by gas chromatography. The results obtained are shown below.

| | |
|---|---|
| Conversion ratio of isobutyraldehyde: | 95.9% |
| Selectivity of CS-12: | 93.2% |
| Yield of CS-12: | 89.4% |

EXAMPLE 20

0.08 g of lithium methoxide (MeOLi, manufactured by Wako Pure Chemical Industries, Ltd.) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 1.5 hours. The reaction mixture after completion of the reaction was analyzed by gas chromatography. The results obtained are shown below.

| | |
|---|---|
| Conversion ratio of isobutyraldehyde: | 92.8% |
| Selectivity of CS-12: | 96.9% |
| Yield of CS-12: | 89.9% |

EXAMPLE 21

0.11 g of sodium t-butoxide (t-BuONa, manufactured by Wako Pure Chemical Industries, Ltd.) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 2.5 hours. The reaction mixture after completion of the reaction was analyzed by gas chromatography. The results obtained are shown below.

| | |
|---|---|
| Conversion ratio of isobutyraldehyde: | 96.5% |
| Selectivity of CS-12: | 92.3% |
| Yield of CS-12: | 89.1% |

EXAMPLE 22

0.11 g of potassium t-butoxide (t-BuOK, manufactured by Wako Pure Chemical Industries, Ltd.) was added to 600 g of isobutyraldehyde and reacted at 40°C. for 1 hour. Subsequently, 0.3 g of barium oxide (BaO, manufactured by Wako Pure Chemical Industries, Ltd.) was added thereto and reacted at 70° C. for 3 hours. The reaction mixture after completion of the reaction was analyzed by gas chromatography. The results obtained are shown below.

| | |
|---|---|
| Conversion ratio of isobutyraldehyde: | 95.1% |
| Selectivity of CS-12: | 93.1% |
| Yield of CS-12: | 88.5% |

EXAMPLE 23

0.06 g of sodium hydroxide (NaOH, manufactured by Wako Pure Chemical Industries, Ltd.) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 3 hours. The reaction mixture after completion of the reaction was analyzed by gas chromatography. The results obtained are shown below.

| | |
|---|---|
| Conversion ratio of isobutyraldehyde: | 82.8% |
| Selectivity of CS-12: | 95.5% |
| Yield of CS-12: | 79.1% |

EXAMPLE 24

0.06 g of potassium hydroxide (KOH, manufactured by Wako Pure Chemical Industries, Ltd.) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 4.5 hours. The reaction mixture after completion of the reaction was analyzed by gas chromatography. The results obtained are shown below.

| | |
|---|---|
| Conversion ratio of isobutyraldehyde: | 90.8% |
| Selectivity of CS-12: | 94.4% |
| Yield of CS-12: | 85.7% |

EXAMPLE 25

0.15 g of sodium oxide ($Na_2O$, manufactured by Aldrich) was added to 600 g of isobutyraldehyde and reacted at 40° C. for 1 hour. Subsequently, 0.3 g of barium oxide (BaO, manufactured by Wako Pure Chemical Industries, Ltd.) was added thereto and reacted at 70° C. for 3.5 hours. The reaction mixture after completion of the reaction was analyzed by gas chromatography. The results obtained are shown below.

| | |
|---|---|
| Conversion ratio of isobutyraldehyde: | 90.3% |
| Selectivity of CS-12: | 92.5% |
| Yield of CS-12: | 83.5% |

EXAMPLE 26

500 g of the reaction mixture obtained in Example 17 was taken, 10 g of water added thereto, and it was rectified by a known method after oil-water separation. The results obtained are shown below.

| | |
|---|---|
| Yield of CS-12: | 425.1 g |
| Rectification efficiency: | 85.0% |

Comparative Example 12

0.6 g of barium oxide (BaO, manufactured by Wako Pure Chemical Industries, Ltd.) was added to 600 g of isobutyraldehyde and reacted at 40° C. for 1 hour. Subsequently, 0.08 g of sodium methoxide (MeONa, manufactured by Wako Pure Chemical Industries, Ltd.) was added thereto and reacted at 70° C. for 3 hours. The reaction mixture after completion of the reaction was analyzed by gas chromatography. The results obtained are shown below.

| | |
|---|---|
| Conversion ratio of isobutyraldehyde: | 55.4% |
| Selectivity of CS-12: | 95.2% |
| Yield of CS-12: | 52.7% |

Industrial applicability

Carrying out various reactions using the base catalysts of the present invention makes it possible to provide a method for producing target compounds at high efficiency, high yield, and low cost, with generation of waste water only in minute amounts, which is very significant in industry. The base catalysts can be used advantageously particularly in a method for producing derivatives of carbonyl compound from carbonyl compounds.

What is claimed is:

1. In a method for producing a glycol monoester from an aldehyde having 2 to 12 carbon atoms in the presence of a catalyst, the improvement wherein the catalyst is a catalyst comprising at least one alkali metal compound selected from the group consisting of alkoxides, hydroxides and oxides of alkali metals, and an alkaline-earth metal oxide, and the method comprises an earlier reaction step using the at least one alkali metal compound and a later reaction step using the alkaline-earth metal oxide.

2. The method as claimed in claim 1, wherein a reaction time for the earlier reaction step is within the range of 0.1 to 2 hours and a reaction time for the later reaction step is within the range of 0.2 to 3 hours.

3. The method as claimed in claim 1, wherein the aldehyde is isobutyraldehyde and the glycol monoester is 2,2,4-trimethyl-1,3-pentanediol monoisobutyrate.

4. In a method for producing a glycol monoester from an aldehyde having 2 to 12 carbon atoms in the presence of a catalyst, the improvement wherein the catalyst is a base catalyst comprising at least one alkali metal compound selected from the group consisting of alkoxides, hydroxides and oxides of alkali metals, and an alkaline-earth metal oxide with a weight ratio of the alkali metal compound to the alkaline-earth metal oxide which is calculated by a formula, "the weight of alkaline metal compound/the weight of alkaline-earth metal oxide", being Prom 0.005 to 1, and the method comprises an earlier reaction step using the at least one alkali metal compound and a later reaction step using the alkaline-earth metal oxide.

5. The method as claimed in claim 4, wherein the weight ratio is within the range of 0.01 to 0.5.

6. The method as claim ed in claim 4, wherein the alkali metal is selected from the group consisting of sodium, potassium, and lithium.

7. The method as claimed in claim 4, wherein the alkaline-earth metal is selected from the group consisting of barium and strontium.

8. The method as claimed in claim 4, wherein an alkyl group in the alkoxide has 1 to 12 atoms.

9. The method as claimed in claim 4, wherein the base catalyst comprises at least one compound selected from the alkali metal alkoxides and at least one compound selected from the alkaline-earth metal oxides.

10. The method as claimed in claim 4, wherein the base catalyst comprises at least one compound selected from the alkali metal oxides and at least one compound selected from the alkaline-earth metal oxides.

11. The method as claimed in claim 4, wherein the base catalyst comprises at least one compound selected from the alkali metal hydroxides and at least one compound selected from the alkaline-earth metal oxides.

12. The method as claimed in claim 4, wherein a reaction time for the earlier reaction step is within the range of 0.1 to 2 hours and a reaction time for the later reaction step is within the range of 0.2 to 3 hours.

13. The method as claimed in claim 4, wherein the aldehyde is isobutyraldehyde and the glycol monoester is 2,2,4-trimethyl-1,3-pentanediol monoisobutyrate.

* * * * *

UNITED STATES PATENT AND TRADEMARK OFFICE
CERTIFICATE OF CORRECTION

PATENT NO. : 6,632,959 B2  
DATED : October 14, 2003  
INVENTOR(S) : Kan-ichiro Inui et al.

It is certified that error appears in the above-identified patent and that said Letters Patent is hereby corrected as shown below:

<u>Column 17,</u>  
Line 10, change "Prom" to -- from --.

<u>Column 18,</u>  
Line 1, change "claim ed" to -- claimed --.  
Line 2, change "12 atoms" to -- 12 carbon atoms --.

Signed and Sealed this

Fifteenth Day of March, 2005

JON W. DUDAS  
*Director of the United States Patent and Trademark Office*

UNITED STATES PATENT AND TRADEMARK OFFICE
CERTIFICATE OF CORRECTION

PATENT NO. : 6,632,959 B2
DATED : October 14, 2003
INVENTOR(S) : Kan-ichiro Inui et al.

It is certified that error appears in the above-identified patent and that said Letters Patent is hereby corrected as shown below:

Column 17,
Line 29, change "Prom" to -- from --.

Column 18,
Line 3, change "claim ed" to -- claimed --.
Line 10, change "12 atoms" to -- 12 carbon atoms --.

This certificate supersedes Certificate of Correction issued March 15, 2005.

Signed and Sealed this

Fourteenth Day of June, 2005

JON W. DUDAS
*Director of the United States Patent and Trademark Office*